United States Patent [19]

Coe et al.

[11] 4,383,990
[45] May 17, 1983

[54] ANTIVIRAL AGENTS, THEIR PREPARATION AND USE

[75] Inventors: Paul L. Coe; Albert S. Jones, both of Birmingham, England; Stewart A. Noble, Boulder, Colo.; Richard T. Walker, Birmingham, England

[73] Assignee: Beecham Group Limited, England

[21] Appl. No.: 303,827

[22] Filed: Sep. 21, 1981

[30] Foreign Application Priority Data

Oct. 1, 1980 [GB] United Kingdom ............... 8031720

[51] Int. Cl.³ .................. A61K 31/70; C07H 19/06
[52] U.S. Cl. ...................................... 424/180; 536/23
[58] Field of Search ................... 536/23, 29; 424/180

[56] References Cited

U.S. PATENT DOCUMENTS 4,247,544  1/1981  Bergstrom ........................ 424/180
4,267,171  5/1981  Bergstrom et al. ............... 424/180

OTHER PUBLICATIONS

Ruth, J. and Bergstrom, D., J. Organic Chemistry, vol. 43, pp. 2870-2876, 1978.
Bergstrom, D. and Ruth, D., J. Am. Chem. Soc., vol. 98, pp. 1587-1589, 1976.
Derwent Abstracts, No. 79101B, Belgium Patent No. 875,773, 1979.
De Clercq et al., Proc. Natl. Acad. Sci., vol. 76, pp. 2947-2951, 1979.

Primary Examiner—Blondel Hazel
Attorney, Agent, or Firm—Jacobs & Jacobs

[57] ABSTRACT

The compound of formula (I):

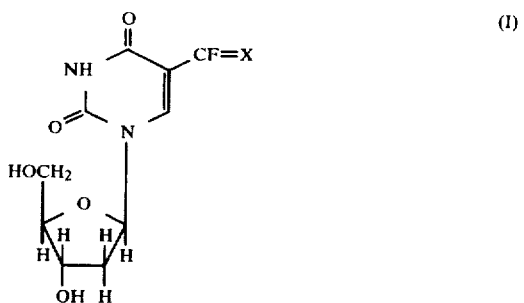

wherein X is CFCl;
and $C_{1-6}$ alkanoyl esters and/or phosphate esters thereof, is active against herpes viruses.

11 Claims, No Drawings

ANTIVIRAL AGENTS, THEIR PREPARATION AND USE

This invention relates to certain fluoro-substituted deoxyuridine compounds which have antiviral activity.

This type of activity has hitherto been demonstrated in a range of deoxyuridine derivatives, such as 2'-deoxy-5-iodouridine (Prusoff & Goz: Handbook of Experimental Pharmacology, Part II of Antineoplastic and Immunosuppressive Agents, pages 272-347) and 2'-deoxy-5-vinyluridine (Cheng et al., Antimicrobial Agents and Chemotherapy, Vol 10, 1, 119-122 (1976).

The activities of these known compounds are not very specific, since they act against several different DNA viruses such as vaccinia and herpes simplex.

More recently, Belgian Pat. No. 875 773 has disclosed 2'-deoxy-5-(2-halogenovinyl)-uridines which have antiviral activity selective against herpes viruses.

We have now discovered a narrow class of fluoro-substituted deoxyuridines which also have antiviral activity against herpes viruses.

According to the present invention there is provided a compound of formula (I)

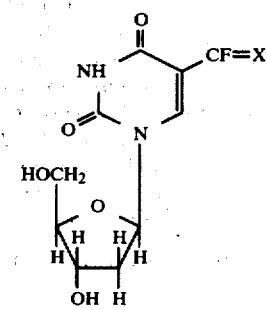

in which X represents CFCl, and $C_{1-6}$ alkanoyl esters and/or phosphates thereof.

The compound of the invention may exist in both the E and Z geometrical forms, and it is to be understood that both geometrical isomers of the compound are included within the scope of this invention, as well as mixtures of the two isomers.

The compound of formula (I) may be separated into the E and Z isomers by hplc as described below in Example 2. Only one of the isomers is active at the levels tested in the screens described below, and this isomer, referred to as "peak 2" (i.e. the second isomer to elute) is preferred. By analogy with other compounds of this general type it is believed that the "peak 2" isomer is the Z isomer, since the Z-isomer generally has the greater activity.

The compound of the invention may be prepared by reacting a compound of formula (II):

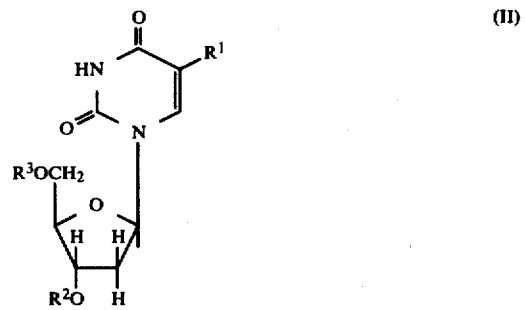

in which $R^1$ is a halogen atom, preferably iodine, and $R^2$ and $R^3$ are hydroxyl protecting groups, with an alkyl lithium compound, preferably n-butyl lithium, to obtain a di-lithium intermediate of formula (IIa):

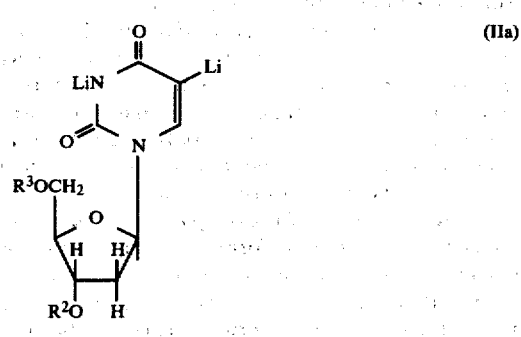

and subsequently reacting the di-lithium intermediate with the halo-substituted ethene of formula (III):

$$F_2C=CClF \quad (III)$$

The complete reaction may be carried out in the same reaction vessel, without isolation of the lithium intermediate. Suitable hydroxyl protecting groups are tri-$C_{1-4}$ alkylsilyl groups, preferably trimethylsilyl groups. Other possible hydroxyl protecting groups are triarylsilyl or aryldialkylsilyl groups.

The reaction is suitably carried out in an inert solvent, such as ether, under an inert atmosphere, preferably nitrogen. In the case when the protecting groups are trialkylsilyl groups, the reaction should be carried out in a dry atmosphere in order to prevent hydrolysis of the trialkylsilyl derivative by atmospheric moisture.

The reaction mixture may be worked up to give a crude product, which can then be purified by chromatography.

The compound of formula (II) in which $R^2$ and $R^3$ each represent an identical trialkylsilyl group may itself be prepared by reacting a 5-halo-2'-deoxyuridine compound of formula (IV):

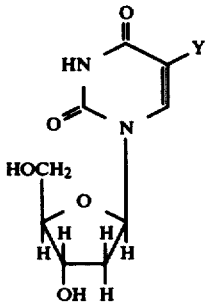

(IV)

in which Y represents a halogen atom with a hexaalkyl-disilazane and trialkylhalosilane, preferably hexamethyldisilazane and trimethylchlorosilane. The reaction is suitably carried out in an organic solvent, preferably dry pyridine.

In a further aspect of the invention, there is provided a pharmaceutical composition which comprises a compound of the formula (I) together with a pharmaceutically acceptable carrier or excipient.

Compositions which may be given by the oral route may be compounded in the form of syrups, tablets and capsules. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the compounds of the invention may be made up into a cream, lotion or ointment. These formulations may be conventional formulations well known in the art, for example, as described in standard books of pharmaceutics and cosmetics, such as Harry's Cosmeticology published by Leonard Hill Books, and the British Pharmacopaeia.

The composition for application to the eyes may be a conventional eye-drop composition well known in the art.

Preferably the compositions of this invention are in unit dosage form or in some other form that the patient may administer to himself a single dose. A suitable dosage unit might contain from 50 mg to 1 g of active ingredient, for example 100 to 500 mg. Such doses may be administered 1 to 4 times a day or more usually 2 or 3 times a day. The effective dose of compound depends on the particular compound employed, but is in general in the range of from 1.0 mg/kg/day to 20 mg/kg of body weight per day or more usually 2.0 mg/kg/day to 10 mg/kg/day.

The present invention also provides a method for treating viral infections of human or non-human animals which method comprises administering an effective, non-toxic amount of a compound of formula (I) to a human or animal having a viral infection.

The following Examples illustrate the invention.

EXAMPLE 1

E/Z-5-(1,2-Difluoro-2-chlorovinyl)-2'-deoxyuridine

To a solution of 5-iodo-2'-deoxyuridine (3.54 g, 10 mmoles) in dry pyridine (50 ml) was added a mixture of hexamethyldisilazane (14.06 ml, $\rho$ 0.765, 10.75 g, 66 mmoles) and chlorotrimethylsilane (7.03 ml, $\rho$ 0.856, 6.01 g, 55 mmoles) over 10 mins. A white suspension formed and this was stirred at room temperature for 15 h. The suspension was removed by filtration through glass fibre at reduced pressure and the filtrate evaporated to give crude 3'5'0-bis(trimethylsilyl)-5-iodo-2'-deoxyuridine.

A solution of n-butyllithium (18.75 ml, 1.6M, 30 mmoles) in n-hexane was added, dropwise over 5 minutes to a stirred solution of the trimethylsilyl derivative in dry diethyl ether at −78° under dry nitrogen. The di-lithium intermediate that formed was insoluble in diethylether and the yellow suspension of the intermediate was treated with an excess of chlorotrifluoroethylene (5.81 g, 50 mmoles). The reaction mixture was stirred for 1 h at −78° and then maintained at that temperature for 4 days. The reaction mixture was then allowed to warm to room temperature and the reaction quenches by the addition of water. Following t.l.c. analysis the ethereal layer was extracted with distilled water twice.

The aqueous layer was neutralised by dilute $H_2SO_4$ and evaporated to dryness. The nucleosidic material was extracted from the insoluble lithium sulphate with methanol and the methonolic residue applied to a silica column. Elution was begun in chloroform/ethanol 9:1 to remove traces of fast running material and then continued in chloroform/ethanol 6:1 to remove 5-trimethylsilyl-2'-deoxyuridine and, immediately afterwards, E/Z-5-(1,2-Difluoro-2-chlorovinyl)-2'-deoxyuridine, and finally with ethanol to remove 2'-deoxyuridine. After pooling the relevant fractions and evaporating the solvent the products were analysed by n.m.r. and the desired product was identified as shown below.

E/Z-5-(1,2-Difluoro-2-chlorovinyl)-2'-deoxyuridine (202 mg, 6%).

N.M.R. Spectrum $\delta$ ($d_6$DMSO) 11.69 (1-H, bd, N-H), 8.48 8.38 (1-H, m, H-6), 6.08 (1-H, m, H-1'), 5.17 (1-H, d, $OH_3$') 5.04 (1-H, m, $OH_5$'), 4.22 (1-H, m, H-3'), 3.79 (1-H, m, H-4'), 3.57 (2-H, m, H-5'), 2.15 (2-H, m, H-2').

$^{19}F$ N.M.R. ($d_6$DMSO, $CFCl_3$ as internal std.)

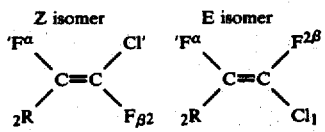

E-isomer $\phi$ 102.7 (1-F, d($J_{\alpha\beta}$=6.5 Hz) $F_\beta$), 122.1 (1-F, dd ($J_{\alpha\beta}$=6.5 Hz, $J_{\alpha H\text{-}6}$=2.3 Hz) $F_\alpha$). Z-isomer 117.4 (1-F, d ($J_{\alpha\beta}$=133.5 Hz, $F_\beta$), 135.9 (1-F, d ($J_{\alpha\beta}$=133.5 Hz, $J_{\alpha H\text{-}6}$=2.3 Hz), $F_\alpha$).

UV Spectrum $\lambda_{max}$ 274.8 nm ($\epsilon$8811), 216 1 nm ($\epsilon$9307), $\lambda_{min}$ 245.8 nm ($\epsilon$3784) at pH 7; $\lambda_{max}$ 274.8 nm ($\epsilon$8361), 216.0 nm ($\epsilon$8834), $\lambda_{min}$ 245.7 nm ($\epsilon$3524) at pH 1; $\lambda_{max}$ 272.8 nm ($\epsilon$6954), $\lambda_{max}$ 230.4 nm (9355), $\lambda_{min}$ 251.8 nm ($\epsilon$5026) at pH 12 in ethanol.

The other products formed were 5-trimethylsilyl-2'-deoxyuridine (200 mg, 7%) and 2'-deoxyuridine (1.40 g, 61%).

EXAMPLE 2

The E and Z isomers of the compound of Example 1 were separated on a Spectra Physics SP 8000 hplc instrument modified to include a fraction-collecting device to semi-automatically collect the two isomers as they were eluted. A Spherisorb 5 ODS column 25 cm in length by 0.8 cm in diameter was used and the isomers eluted using 75% v/v 0.05 M aqueous ammonium acetate (pH 4.2) and 25% v/v methanol at a flow rate of 25 ml/min at 25° C.

The first isomer to elute ("peak 1") had a retention time of 680 seconds and the second isomer ("peak 2") had a retention time of 830 seconds.

ANTIVIRAL ACTIVITY

In Vitro

Method

Vero (African Green Monkey Kidney) cells were grown to confluence in 6 well multidishes, each well being 3.5 cm in diameter. The cells were incubated with Herpes simplex type 1 virus (HFEM strain) and overlaid with 0.5 mL of 0.9% agarose (w/v) in maintenance medium containing the test compound at a range of concentrations from 200 µg/mL in half-log dilution steps. The virus infected cultures were then incubated at 37° C. for 6 days before fixing in 4% formaldehyde solution and staining with carbolfuchsin. The dishes were then examined to find that concentration of test compound causing a 50% reduction in the number of virus plaques formed ($PDD_{50}$ value) and the minimum concentration of test compound which killed the cell monolayer, leaving a clear zone devoid of cells and virus plaques (MTD).

The same method was used to determine the $ED_{50}$ (concentration reducing the plaque number at 50%) of the E/Z mixture against the KOS and SK16 strains of Herpes simplex virus type 1 and the $ED_{50}$ of the E/Z mixture and the separated isomers ("peak 1" and "peak 2") against the HFEM strain. Results are given in Table 1.

Results

E/Z-5-(1,2-Difluoro-2-chlorovinyl)-2'-deoxyuridine had a $PDD_{50}$ of 14 µg/mL and its MTD was >200 µg/mL. In comparison, the clinically useful antiherpes agent 5-iodo-2'-deoxyuridine had a $PDD_{50}=3$ µg/mL and its MTD was >100 µg/mL.

TABLE 1

| Compound | HSV-1 strain | $ED_{50}$ (µg/ml) |
|---|---|---|
| E/Z | KOS | 20 |
| E/Z | SC16 | 21 |
| E/Z | HFEM | 24 ± 3 |
| "Peak 1" | HFEM | >100 |
| "Peak 2" | HFEM | 24 ± 6 |

ANTI-HOST CELL ACTIVITY

Vero cells seeded at low density were grown in the presence of E/Z-5-(2-chloro-1,2-difluorovinyl)-2'-deoxyuridine for 72 h. During this time the cells doubled in number approximately once every 24 h. Even at a compound concentration on 100 µg/ml only slight depression of cell growth was observed. 5-(2-Chloro-1,2-difluorovinyl)-2'-deoxyuridine thus has a therapeutic ratio of >5.

Tests were also carried out using the human diploid fibroblast MRC-5 cell line, and again E/Z-5-(2-chloro-1,2-difluorovinyl)-2'-deoxyuridine had little effect on cell proliferation, even at 200 µg/ml.

We claim:

1. A compound of formula (I):

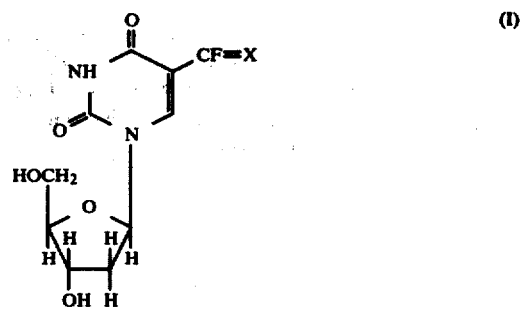

wherein X is CFCl.

2. A compound of formula (I) as claimed in claim 1 in an optically pure form having a retention time of 830 seconds on a 25 cm length, 0.8 cm inner diameter, h.p.l.c. column, packed with Spherisorb S ODS when eluted with methanol in aqueous ammonium acetate (0.05 M), the volume of solvents being in a ratio of 1 to 3, at 25° C., and at a flow rate of 25 ml.min$^{-1}$.

3. The Z-isomer of the compound (I) of claim 1.

4. A process for producing a compound of formula (I) as defined in claim 1 which process comprises reacting a compound of formula (II):

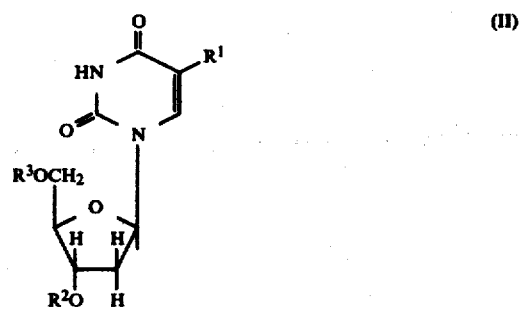

wherein $R^1$ is a halogen, and $R^2$ and $R^3$ are hydroxyl protecting groups, with an alkyl lithium to obtain a compound of formula (IIa):

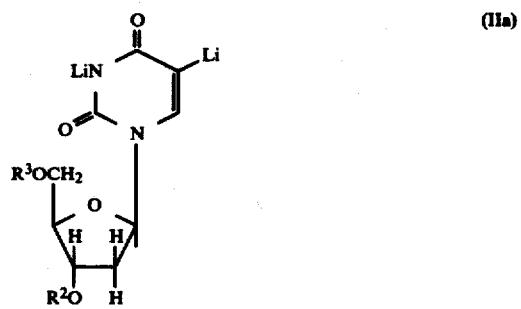

and subsequently reacting the compound of formula (IIa) with the compound of formula (III):

$F_2C=CCl.F$ (III).

5. A process as claimed in claim 4 wherein $R^1$ is iodine.

6. A process as claimed in claim 4 wherein the alkyl lithium compound is n-butyl lithium.

7. A process as claimed in claim 4 wherein the hydroxyl protecting groups are tri($C_{1-4}$)-alkylsilyl groups.

8. A pharmaceutical composition having antiviral activity against herpes viruses comprising an anti-viral effective amount of a compound of formula (I) according to claim 1 in combination with a pharmaceutically acceptable carrier or excipient.

9. A composition as claimed in claim 8 in unit dosage form comprising from 50 mg to 1 g of the compound of formula (I) per unit dose.

10. A method for treating herpes viral infections of human or non-human animals which method comprises administering an effective, non-toxic amount of a compound of formula (I) according to claim 1 to a human or non-human animal having a herpes viral infection.

11. A method according to claim 10 comprising administering from 1.0 to 20 mg of compound/kg of bodyweight per day.

* * * * *